(12) United States Patent
Pratt et al.

(10) Patent No.: US 9,689,833 B2
(45) Date of Patent: Jun. 27, 2017

(54) AUXILIARY MICRO-ELECTRODES FOR DIAGNOSTICS OF ELECTROCHEMICAL GAS SENSORS

(71) Applicant: LIFE SAFETY DISTRIBUTION AG, Uster (CH)

(72) Inventors: Keith Francis Edwin Pratt, Portsmouth (GB); Martin G. Jones, Havant (GB); John Chapples, Portsmouth (GB); Lei Xiao, London (GB)

(73) Assignee: Life Safety Distribution AG, Uster (CH)

( * ) Notice: Subject to any disclaimer, the term of this patent is extended or adjusted under 35 U.S.C. 154(b) by 862 days.

(21) Appl. No.: 13/644,485

(22) Filed: Oct. 4, 2012

(65) Prior Publication Data
US 2013/0087456 A1    Apr. 11, 2013

Related U.S. Application Data

(60) Provisional application No. 61/545,669, filed on Oct. 11, 2011.

(51) Int. Cl.
*G01N 27/404*    (2006.01)
*G01N 27/416*    (2006.01)

(52) U.S. Cl.
CPC ....... *G01N 27/404* (2013.01); *G01N 27/4163* (2013.01)

(58) Field of Classification Search
CPC ......... G01N 27/404–27/4045; G01N 27/4062; G01N 27/4065; G01N 27/4163; B01D 53/32–53/326
See application file for complete search history.

(56) References Cited

U.S. PATENT DOCUMENTS

| | | | |
|---|---|---|---|
| 5,423,963 A | 6/1995 | Fletcher et al. | |
| 5,558,752 A | 9/1996 | Wang et al. | |
| 5,668,302 A | 9/1997 | Finbow et al. | |
| 5,723,036 A | 3/1998 | Chrzan et al. | |
| 5,932,079 A * | 8/1999 | Haupt et al. | 204/415 |

(Continued)

FOREIGN PATENT DOCUMENTS

| | | |
|---|---|---|
| DE | 195 33 911 C1 | 5/1996 |
| DE | 19533911 C1 | 5/1996 |

(Continued)

OTHER PUBLICATIONS

European Search Report, dated Jul. 11, 2013, corresponding to Application No. EP 12 18 7534.

(Continued)

*Primary Examiner* — Luan Van
*Assistant Examiner* — Maris R Kessel
(74) *Attorney, Agent, or Firm* — Conley Rose, P.C.; Kristin Jordan Harkins (57) ABSTRACT

A gas sensor includes known types of electrodes such as sensing electrodes, counter electrodes or reference electrodes to sense the presence of a predetermined gas. In addition, at least one diagnostic electrode is carried in the sensor. The diagnostic electrode implements at least one diagnostic function without substantially impairing the gas sensing function. The diagnostic electrode is immersed in sensor electrolyte.

18 Claims, 7 Drawing Sheets

(56) References Cited

U.S. PATENT DOCUMENTS

| | | | |
|---|---|---|---|
| 6,096,186 A | 8/2000 | Warburton | |
| 6,251,243 B1 | 6/2001 | Lindsay | |
| 6,562,208 B2 | 5/2003 | Slater et al. | |
| 2002/0036137 A1 | 3/2002 | Slater et al. | |
| 2008/0202929 A1 | 8/2008 | Chapples et al. | |
| 2009/0127134 A1 | 5/2009 | Pratt et al. | |
| 2010/0252455 A1 | 10/2010 | Pratt et al. | |
| 2011/0100813 A1* | 5/2011 | Davis et al. | 204/415 |
| 2012/0193229 A1 | 8/2012 | Tillotson et al. | |

FOREIGN PATENT DOCUMENTS

| | | |
|---|---|---|
| EP | 2 327 981 A2 | 7/2011 |
| EP | 2591734 B1 | 2/2017 |
| WO | WO 99/24826 | 5/1999 |
| WO | WO 01/31326 A1 | 5/2001 |

OTHER PUBLICATIONS

Partial European Search Report, dated Feb. 5, 2013, corresponding to Application No. EP 12 18 7534.
Europe Patent Application No. 12187534.8, Examination Report dated Jul. 30, 2013, 14 pages.
Europe Patent Application No. 12187534.8, Examination Report dated Apr. 9, 2015,5 pages.
Europe Patent Application No. 12187534.8, Communication Under Rule 71(3) EPC, dated Oct. 4, 2016, 37 pages.
Europe Patent Application No. 12187534.8, Decision to Grant, dated Jan. 12, 2017, 2 pages.

* cited by examiner

AUXILIARY MICRO-ELECTRODES FOR DIAGNOSTICS OF ELECTROCHEMICAL GAS SENSORS

CROSS-REFERENCE TO RELATED APPLICATION

This application claims the benefit of the filing date of U.S. Provisional Application Ser. No. 61/545,669 filed Oct. 11, 2011, entitled, "Auxiliary Electrodes for Diagnostics of Electrochemical Gas Sensors". The '669 application is hereby incorporated herein by reference.

FIELD

The application pertains to gas sensors which include extra electrodes to carry out diagnostics of the respective sensor. More particularly, the application pertains to additional small, or, micro-electrodes incorporated in electrochemical gas sensors to carry out diagnostic activities while the respective sensor is in operation.

BACKGROUND

Electrochemical sensors are known and can be used to detect various types of gases including oxygen as well as toxic gases such as carbon monoxide, sulphur dioxide and hydrogen sulfide. Representative sensors have been disclosed in U.S. Pat. No. 5,668,302 to Finbow et al. entitled "Electrochemical Gas Sensor Assembly", issued Sep. 16, 1997, and U.S. Patent Application No. 2010/0252455 published Oct. 7, 2010 and entitled "Methods of Operation of Electrochemical Gas Sensors". Both the '302 patent and the '455 application are commonly owned with the present application and are incorporated herein by reference.

It is advantageous to provide means of performing diagnostic tests of various types on electrochemical gas sensors to detect such effects as end of life, change in electrolyte concentration, incorrect/faulty operation, etc. Currently such tests are often performed by modulating the sensing electrode and monitoring the resulting signal. For example, U.S. Pat. No. 6,251,243 describes a method by which the transient signal resulting from a perturbation to the sensing electrode is used to determine if the sensor is operating correctly.

EP 2327981 describes a technique whereby the sensing electrode signal is interrupted to generate a diagnostic. U.S. Pat. Nos. 5,558,752 and 6,096,186 describes a means whereby the sensing electrode potential is scanned to measure electrode activity. Methods such as those described above all potentially suffer from the disadvantage that by perturbing the sensing electrode the sensor may be out of operation for the duration of the test and also may require considerable time (in some cases many hours) to recover back to normal operation following the test. Furthermore, due to the high surface area of typical gas diffusion electrodes any such tests (e.g. scanning voltammetry) need to be performed relatively slowly. This again may result in the sensor being out of use for several hours. As a result such tests can only be performed infrequently, or when the sensor is not in use. For many applications, however, it is desirable to be able to carry out diagnostics much more rapidly and/or frequently.

DETAILED DESCRIPTION

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In summary, embodiments hereof incorporate one or more additional micro-electrodes into an electrochemical gas sensing cell for the purposes of cell diagnostics. The sensor may have a two or more electrode amperometric design. The diagnostic electrode(s) does not interfere with the normal sensor operation. The diagnostic electrode(s) is/are immersed in an electrolyte and are not in direct communication with the incoming target gas passing through the diffusion barrier controlling access to the cell.

We therefore propose the use of one or more separate diagnostic electrodes. Such electrodes can be configured to avoid interrupting the gas measurement or disrupting the normal operation of the device. These electrodes are included in the sensor in addition to two or more electrodes which form part of the sensor's gas sensing structure. To ensure that the sensor can still operate during the diagnostic, which can be performed quickly and/or continuously in a manner which does not interfere with the other electrodes, it is preferable that the diagnostic electrode(s) should be of small surface area compared to the sensing electrode so that current passed does not significantly disturb the sensing electrode and voltage sweeps (for example) can be performed rapidly. Non-exclusive examples of the sensor failure modes which this approach can help to identify are described below.

Sensing electrode applications: a majority of electrochemical gas sensors operate on the principle that all target gas entering the sensor through the gas diffusion limiting feature (e.g. the capillary or solid membrane barrier) is consumed by the sensing electrode. It is normal to design the sensing electrode with spare capacity to ensure that this condition is met since it is not possible to directly relate the sensor output to the external atmospheric concentration without this condition being maintained. However, under conditions of overload (high target gas concentration) or loss of catalytic activity, even effective, normally operating sensors may be overwhelmed and move out of the diffusion limited mode.

A diagnostic electrode placed inboard of the sensing electrode can readily detect the presence of species (for example the target gas, interfering gas or pollutant) being transmitted through or otherwise bypassing the sensing electrode and so flag a potentially hazardous condition by producing a diagnostic signal which is coupled to associated control circuits. The control circuits, in response to the diagnostic signal(s) can adjust operating conditions at the sensor and/or transmit warning or information signals to remote monitoring stations.

The methods may also be used to detect species reaching the electrode from routes other than via the normal diffusion limited gas access. Examples include gas accessing the sensor through vents or other pressure release means; gas gaining access through damaged or leaking housings, or unintentional leak paths; or reaction products from known or unexpected cell reactions, e.g. oxygen evolved from the counter electrode in an oxygen pump sensor.

Drying out of sensors based on aqueous electrolytes is another key failure mode. The techniques described herein may also be used to detect the degree of hydration in electrolyte in contact with or near to the sensing electrode.

The same diagnostic electrode can also be used to generate the target or a surrogate test gas, for example hydrogen or oxygen, to provide a stimulus to the sensing electrode. This test signal will then appear superimposed on the normal output. It can then be responded to by the respective control circuits.

Reference electrode applications: in addition to tests of the sensing electrode, there are other important failure modes which can be detected with additional diagnostic electrodes. A key design and operational aspect of amperometric electrochemical devices such as sensors is the requirement for means to monitor and/or control the operating potential of their working electrode(s). The potential has a critical impact on the reactivity of species reaching the electrode. Thus, gas sensors, particularly 3 electrode types, require a stable, reliable reference electrode for correct operation. (The reference electrode may be a combined pseudo reference/counter in a 2 electrode sensor or a separate reference electrode in a 3 or 4 electrode sensor).

In laboratory based experiments this is typically performed by using a reference electrode which has a well-defined and stable electrochemical potential, such as a dynamic hydrogen electrode (DHE), saturated calomel electrode etc. Such electrodes are however not normally used in low cost commercial sensors due to such factors as size, cost, complexity, toxicity, etc. It is common practice instead to use pseudo reference electrodes.

For example platinum is often used as a pseudo reference electrode in sulfuric acid based gas sensors, as it has a potential determined by the pH and a logarithmic function of oxygen concentration in the vicinity of the electrode, for example as in the 4CM Carbon Monoxide sensor, City Technology Ltd. This produces a reasonably well defined and stable potential under certain conditions. However, excessively low/high oxygen concentrations near the reference electrode can result in a shift or drift of the reference potential and incorrect operation of the sensor. This issue also affects oxygen pump sensors. The methods described here allow the measurement of oxygen concentration in the electrolyte in the vicinity of the reference electrode.

If the oxygen environment near the reference electrode is being measured then a correction to the operating bias of the sensor can be applied to correct for the effect of oxygen concentration on the reference potential. Alternatively, the sensor can flag that the reference is moving outside the acceptable operating range and request remedial action.

There are other effects which can cause reference potential drift—dissolved gases other than oxygen; electrode poisoning; pH shifts, etc. Furthermore, platinum does not have such a clearly defined reference potential with other electrolytes. There are, for example, benefits in using alkaline electrolytes in certain sensors, (particularly oxygen pumps) or using ionic liquids which can offer improved performance in humidity extremes. Commonly used reference electrodes in alkaline electrolytes include Calomel (mercury chloride) and Mercury/Mercury oxide—both of which are unacceptable for environmental and health and safety reasons. In other systems it is common practice in a laboratory setting to use a silver wire as a pseudo reference and to calibrate this against a known redox couple, such as ferrocine, dissolved in the electrolyte. Again, this is an undesirably complex process. There is a clear requirement for simple and reliable methods to measure and correct for drifts in gas sensors caused by such mechanisms.

Embodiments hereof avoid the need for a reference electrode and separate calibration step by performing a measurement such as cyclic voltammetry on a microelectrode in the sensor, measuring the redox potential from the voltammogram and using this to adjust the potential applied between sensing and counter electrodes in the sensor, to maintain the correct electrochemical potential of the sensing electrode. The microelectrode may operate by measuring a redox couple such as ferrocine/ferricinium dissolved in the electrolyte, or may use a feature of the electrolyte itself such as the hydrogen peaks observed in voltammetry of aqueous acids on platinum electrodes. These methods provide alternative intermittent determinations of reference electrode drift in the continuously operating conventional reference. Such approaches can also be used in conjunction with the pseudo-reference/counter electrode in a 2 electrode cell to measure & compensate for drift in the reference potential.

As noted above, dynamic hydrogen electrodes (DHE) are generally too bulky to be used as the reference electrode in a gas sensor. (The DHE is effectively a metal electrode, such as platinum, which generates hydrogen by electrolysis by a small current passed through it, the resulting hydrogen covered platinum acts as a very stable reference). However, we have recognized that basing a DHE on a microelectrode as described here allows this method to also be employed as an intermittent means of checking for drift in the potential of the existing reference electrode.

Counter electrode applications: electrochemical sensors for toxic gases typically rely on the reduction of oxygen as the counter electrode reaction. Oxygen is normally present in the ambient air and/or dissolved in the sensor electrolyte at sufficiently high concentration for the counter reaction to proceed. However if, for whatever reason, the oxygen concentration near the counter electrode is inadequate then the counter reaction may become the limiting step (resulting in slow or reduced target gas response) or in extreme cases could result in the sensor failing to respond to the target gas at all. These failure modes are potentially unsafe as the sensor baseline will be unaffected, and correct operation can typically only be confirmed by bump testing with a gas. Some causes of inadequate oxygen concentration at the counter electrode include prolonged operation in low or zero ambient oxygen concentrations, or exposure to overload concentrations of target or interferent gases resulting in excessive consumption of oxygen by the counter electrode.

Embodiments hereof use an additional micro-electrode to measure the oxygen concentration in the vicinity of the counter or combined pseudo-reference/counter to check that there is sufficient oxygen present for correct operation. Signals from that electrode can be used to warn that the sensor is no longer working correctly. Alternatively the measured oxygen concentration near the counter electrode could be used to apply a correction to the sensor signal.

In an oxygen pump, such a measurement is also of value, for example to determine whether the electrolyte in the vicinity of the counter is in danger of becoming saturated, so increasing the risk of counter failure, or to detect blockage of the vent leading to oxygen build up in the sensor.

Electrolyte applications: a number of other diagnostic tests relate particularly to the cell electrolyte. A key issue is whether electrolyte is present in sufficient concentrations at key locations to support proper cell operation. For example, microelectrodes can be used to map the location and concentration of electrolyte (e.g. by conductivity measurements). Similarly, the presence of organic contaminants within the electrolyte can be detected by running voltammetric sweeps with suitable positioned microelectrodes.

Embodiments of the invention use a separate electrode or electrodes to perform diagnostics so as to avoid disturbing the operation of the sensing electrode(s) or other electrodes within the sensor. Thus, the use of one or more separate diagnostic micro-electrodes avoids interrupting the gas measurement and the sensor can still operate normally during the diagnostic process. The diagnostic process can be performed quickly and/or continuously by virtue of the fact that the diagnostic electrodes are of a form that allows them to operate without interfering with the other electrodes. Embodiments of sensors in accordance herewith exhibit other beneficial properties as described below.

Diagnostic micro-electrode(s) in accordance herewith will preferably have at least some of the following exemplary properties. Such electrodes should be of sufficiently small surface area compared to the sensing electrode so that current passing through the diagnostic probe does not significantly disturb the sensing electrode. Such electrodes will preferable have a surface area which is small enough to allow diagnostic processes such as voltammetry to be performed sufficiently rapidly (e.g. by minimizing charging currents due to double layer capacitance). Although the intention is that normal sensor operation may proceed unimpeded during the diagnostic process, sensor users will not accept very slow responding methods.

A further benefit of using a small electrode is that it may have microelectrode properties of radial diffusion. Preferably, the electrode(s) will have microelectrode dimensions in at least one or two of its dimensions. For example, the diagnostic electrode may be either a bare wire which can act as a microcylinder electrode, or a suitably insulated wire with exposed tip which can act as a microdisc electrode, or any other design which provides microelectrode type behavior, for example an array of electrodes such as a microband or microdot arrays. Embodiments incorporating such microelectrodes can support various types of diagnostics as described below, and come within the spirit and scope of the invention.

Embodiments hereof can be used in making localized measurements of electrolyte conductivity to map the behavior at key locations in the sensor. The particular advantage of the microelectrode in this context is that it provides a more localized measurement relating to the vicinity of the electrode rather than an averaged measurement of the type provided between larger electrodes. An example of where this difference could be important is in the case of an electrode and/or separator which becomes selectively dried out in certain regions, e.g. where the target gas enters the cell. This can significantly affect sensor performance under conditions where the 'averaged' behavior appears to be satisfactory.

Alternately, by performing cyclic voltammetry of the microelectrode (which may be for example a platinum microdisc or cylinder) against the existing sensor reference electrode, the resulting voltammogram can be processed to determine the potential difference between the sensing electrode and the redox potential measured by the microelectrode. The use of a microelectrode allows very fast scanning (milliseconds) and hence fast adjustment to be performed, with low power. If very fast feedback is required then a separate pseudo-reference electrode could still be included (making 4 electrodes in total) with the microelectrode being used to make slower trim adjustments for drift in the pseudo reference electrode.

Figure 1:
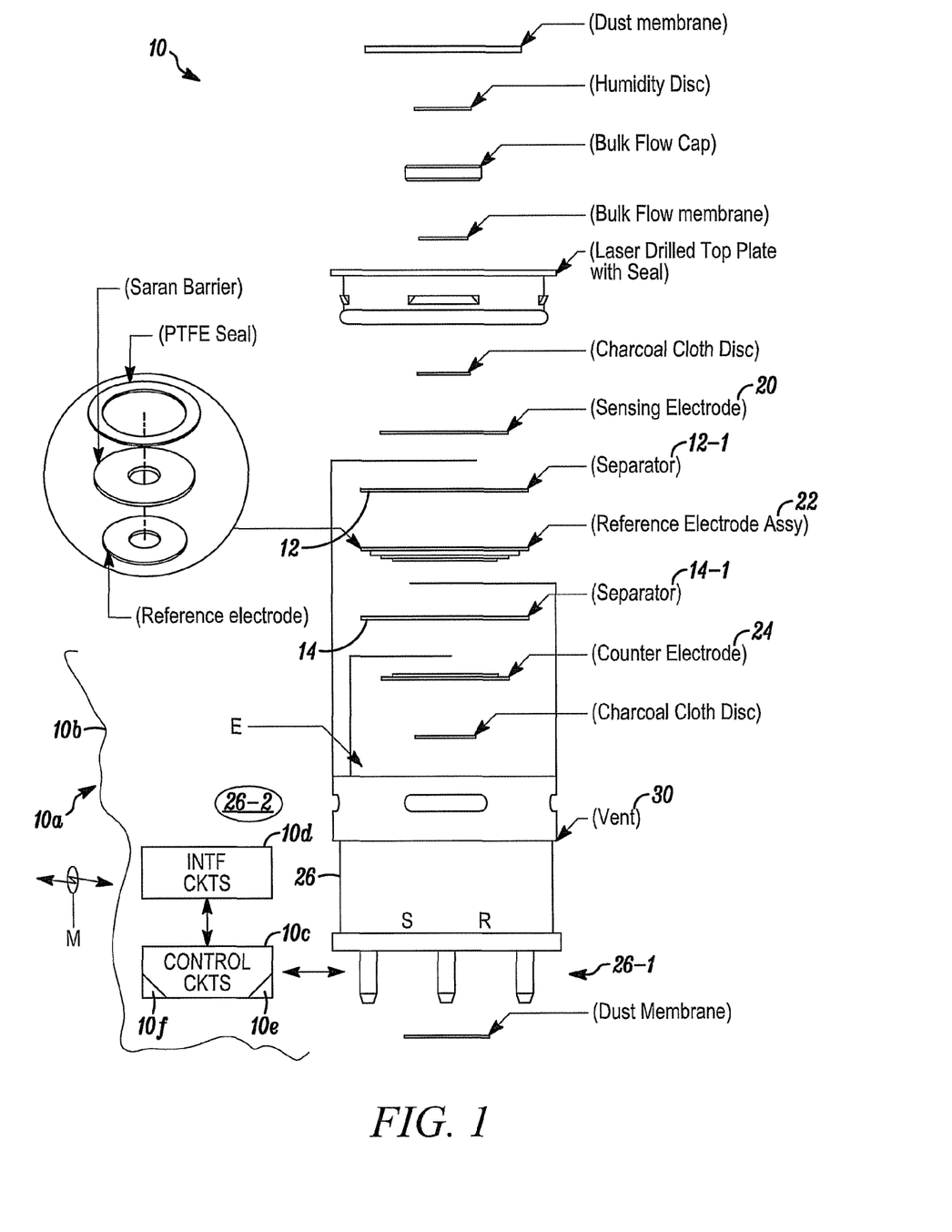
FIG. 1 illustrates an exploded view of a gas sensor accordance herewith.

With respect to the Figures, FIG. 1 illustrates an exemplary embodiment of a gas sensor 10. FIGS. 2-7 illustrate aspects of exemplary diagnostic methods that can be carried out by sensors having micro-electrodes as discussed herein.

FIG. 1 illustrates an exploded view of an exemplary oxygen pump sensor 10, with diagnostic micro-electrodes 12, 14, used to carry out the below described experiments. Microelectrodes 12, 14 are installed in sensor 10 at the positions shown at separator 12-1 near the sensing electrode 20, and at separator 14-1 between the reference and counter electrodes 22, 24.

Electrolyte E is contained in the housing 26. Electrodes 12, 14 are immersed in the electrolyte E, and are not in the direct path of the target gas.

The above described electrodes such as 12, 14, 20, 22, 24 along with the electrolyte E are carried in a housing 26. Housing 26 can include a vent 30 as would be understood by those of skill in the art. Sensor 10 can be carried by a gas detector 10a, in an external housing 10b.

Electrical connecting elements, indicated at 26-1, carried by housing 26 are coupled to the various electrodes in the housing 26. A power supply 26-2, which could be implemented as a rechargeable battery, could be carried in housing 10b to energize the detector 10a.

Housing 10b can also carry control circuits 10c which are coupled to the connector elements 26-1 to receive signals from and coupled signals to the electrodes 12, 14, 20, 22, 24 so as to sense conditions in the sensors 10, or to control the operation of one or more electrodes to carry out the operational and diagnostic methods described herein.

The detector 10a can communicate via interface circuits 10d, coupled to control circuits 10c, via a medium M (which could be wired, or wireless), control circuits 10c with displaced monitoring systems. The control circuits can be implemented, at least in part, with a programmable processor 10e which executes pre-stored control instructions 10f. Other elements of the sensor 10, illustrated in FIG. 1, are conventional and would be known to those of skill in the art.

Exemplary microelectrodes can be fabricated from PTFE (polytetrafluoroethylene) coated platinum wire (Advent research materials part number PT5431, comprising 75 um diameter platinum wire with approximately 18 um thick PTFE coating). The wire can be cut with a scalpel to produce a microdisc electrode inside the sensor 10, and the PTFE insulation stripped from the end of the wire external to the sensor to allow electrical contact to be made. The exposed tip of the wire can be pushed into the respective separator 12-1, 14-1 to avoid it shorting against the adjacent electrode 20, 24. However an alternative approach includes sandwiching the microelectrodes 12, 14 between two separators. Other configurations come within the spirit and scope of the invention.

Electrochemical measurements were performed using a Biologic VMP3 multichannel potentiostat using two channels configured as a bipotentiostat. Both the sensing electrode 20 and diagnostic electrode(s) 12, 14 would be operated with respect to the existing counter and reference electrodes in the sensor.

Figure 2:
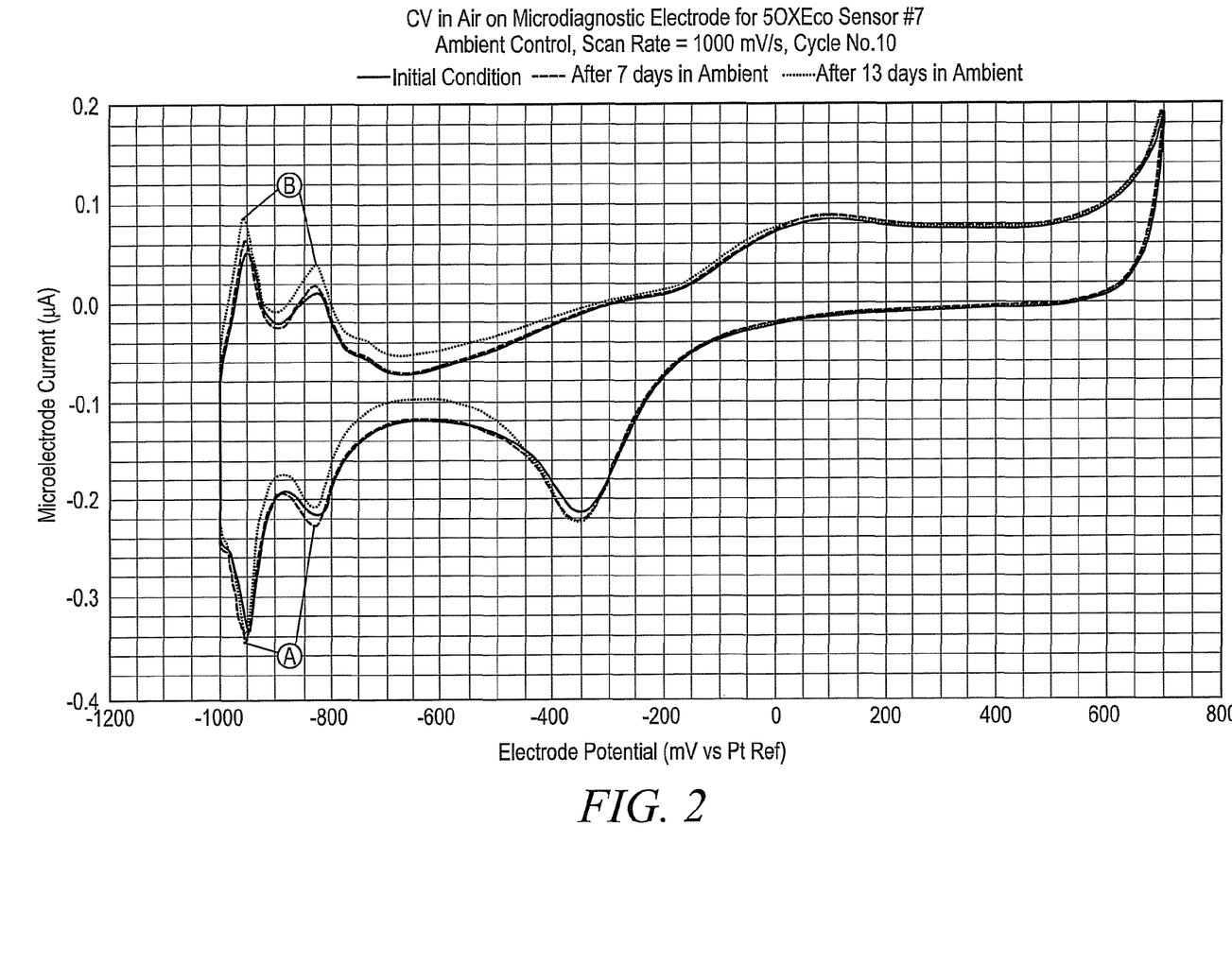
FIG. 2 illustrates a graph of current vs. potential of a micro-electrode in accordance herewith.
Figure 3:
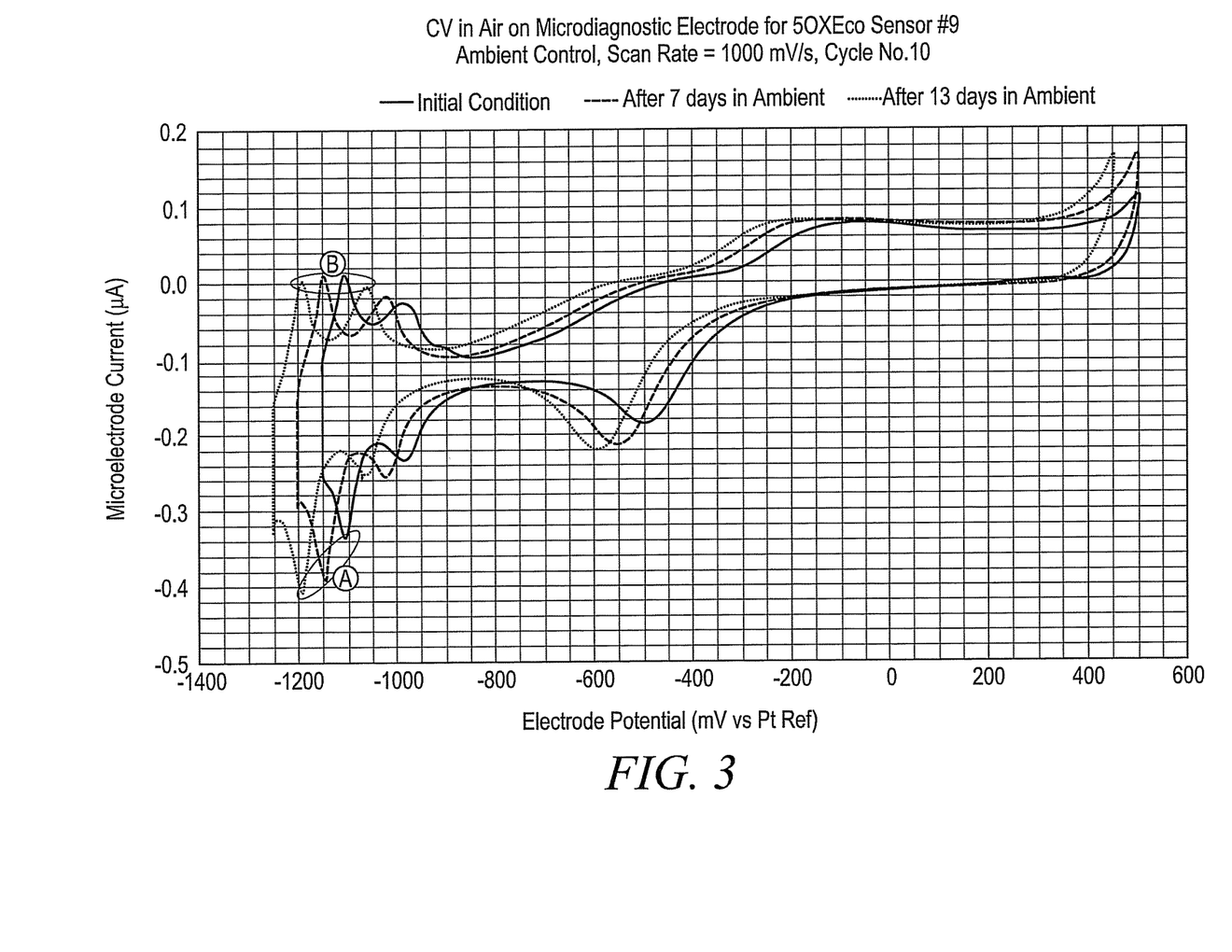
FIG. 3 is another graph of current vs. potential of a micro-electrode in accordance herewith.

FIGS. 2 and 3 illustrate the voltammetry of a platinum micro-electrode 12 located near to the sensing electrode 20. It will be understood that the actual location of the microelectrode is not critical, unless the intention is to measure I/R (infrared) drop within the sensor. As in FIGS. 2, 3 characteristic pairs of peaks are observed for adsorbed hydrogen generation (A) and corresponding stripping (B). The absolute electrochemical potentials at which these peaks occur are well defined. Voltammetry was performed by repeatedly scanning the electrode potential, relative to the platinum pseudoreference electrode, between −1000 mV and +700 mV at a rate of 1000 millivolts per second.

In practice it is not necessary to perform the full potential scan shown in FIGS. 2 and 3 if only the hydrogen peaks need to be observed, the scan can instead be limited to the region around the peaks.

Both FIGS. 2 and 3 illustrate the diagnostic performed on freshly made sensors and then after 7 and 13 days operation. FIG. 2 illustrates a 'good' sensor which exhibited stable performance. Conversely FIG. 3 illustrates a 'bad' sensor whose performance drifted over time, specifically in terms of its speed of response eventually slowing down due to a shift in the operating potential of its pseudo reference electrode. The shift in potential of the reference electrode can clearly be seen by the progressive shift in positions of the hydrogen peaks in FIG. 3. The shift in the peaks was detected before the sensor measurably started to slow down, making it a useful early warning diagnostic. This diagnostic method could be used to trigger remediation action such as the technique described herein or a correction applied to the sensing electrode bias voltage to compensate for drift in the reference potential.

Figure 4:
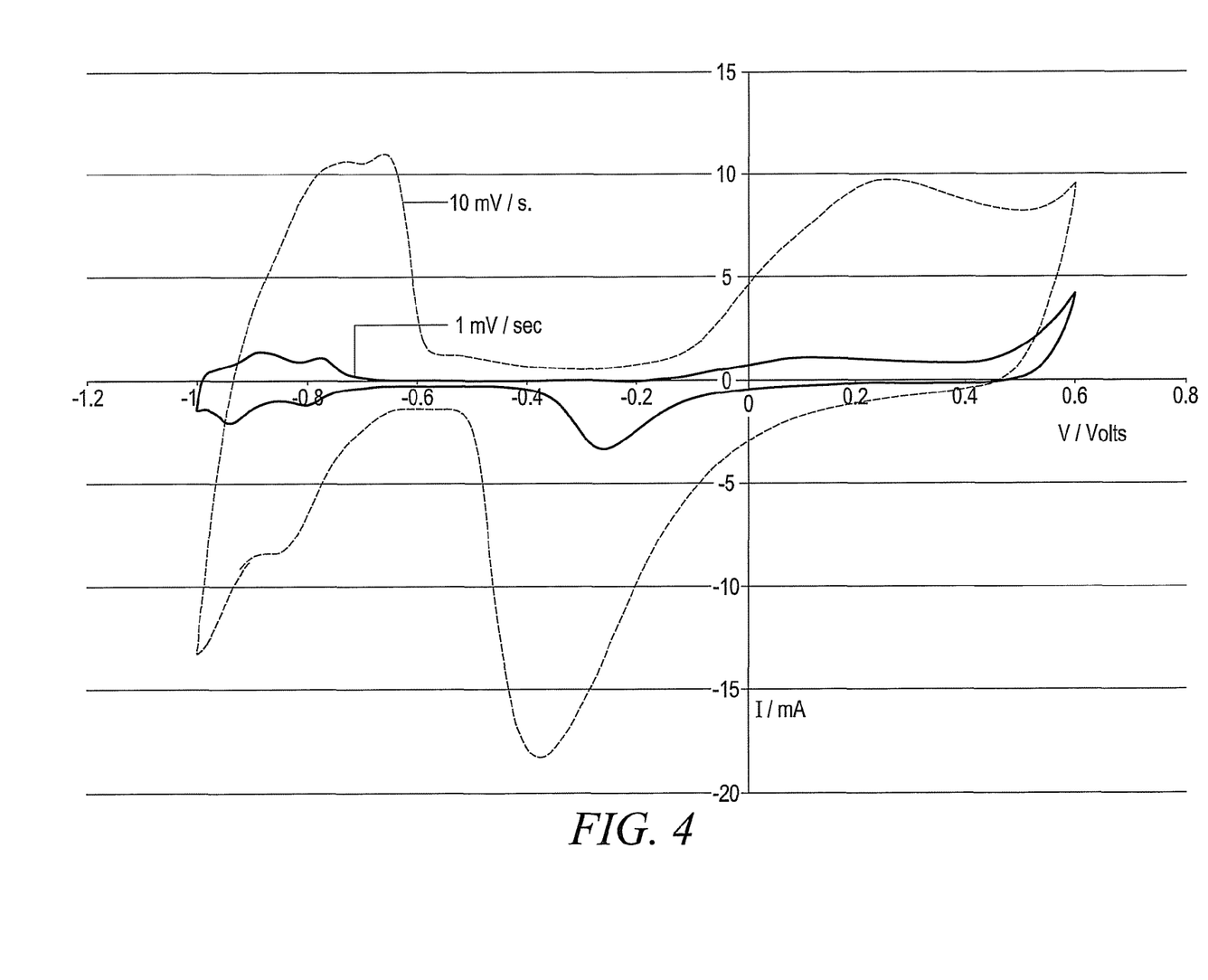
FIG. 4 illustrates results of an alternate measuring approach.

For comparison, FIG. 4 illustrates the detection of these peaks performed by scanning the potential of the platinum sensing electrode in a sensor of the same type without a diagnostic microelectrode. This is a valid means of performing a reference potential measurement. It has the following characteristics.

The sensing electrode is taken out of use while the measurement is being performed meaning that alternative arrangements must be made to provide gas detection in safety critical applications.

Due to the typically very high surface area and hence large double layer capacitance of gas diffusion electrodes, it is necessary to perform a very slow scan otherwise charging currents swamp the desired measurement. The scan rates used for the two traces are 1 millivolt per second and 10 millivolts per second. It can be seen that the hydrogen peaks are less well defined, and also there is some shift between the hydrogen generation (A) and stripping (B) peaks resulting in inaccuracy in the measured potential. The slow scan rates required to perform this test on the sensing electrode results in the entire measurement taking several minutes or even hours. Since the sensing electrode is exposed to the ambient environment, changes in the environment, for example the target gas, can result in additional signals which would need to be deconvoluted from the desired signal.

FIG. 4 illustrates that the currents generated during the scan are milliamps to tens of milliamps, resulting in quite high power requirements during the scan. These require specific circuit design to ensure that they are properly handled and contribute to an undesirable power drain (especially since many sensors of this type are used in portable instruments where battery life is critical). Note that in FIGS. 2, 3, the currents are lower by a factor of at least $10^4$.

There are various options for electrochemical features which can be used as well defined referenced points in addition to the absorbed hydrogen peaks demonstrated above. For example, an electrochemically active redox species such as ferrocine or ferrocyanide can be added to the electrolyte to produce suitable voltammetric features. This approach is particularly useful when employing hydrophobic electrolytes in which hydrogen evolution is difficult or impossible due to the low water content.

Dissolved species can be detected in the electrolyte using sensors in accordance herewith. In the case of dissolved oxygen, the diagnostic electrode would typically be a platinum electrode operating at a potential where it can reduce oxygen and generate a current proportional to the oxygen concentration. Ideally it should be a small electrode (such as a wire or microdisc electrode) for a number of reasons: (1) it is not desirable for the diagnostic electrode to consume too much oxygen (and hence exacerbate the very issue it is trying to detect). (2) Its current should be low so as to minimize power requirements and minimize interference with the general sensor operation. (3) It is beneficial for it to have microelectrode radial/spherical diffusion properties so as to allow a quantitative steady state measurement of oxygen concentration. The diagnostic electrode may be operated continuously, intermittently or have its potential stepped or cycled using any of the techniques known to those in the field of electrochemistry.

Measuring breakthrough of the target or interferent gas from the sensing electrode (which may occur for example under conditions of overload or loss of sensing electrode activity) can be valuable in determining whether the sensor is still operating in the required diffusion limited mode.

For example, in oxygen pump sensors, we have induced a loss in sensing electrode activity by either 'switching off' the sensing electrode (i.e., allowing it to go open circuit) or by biasing it to a less active potential. Under these conditions, a microelectrode positioned inboard of and near to the sensing electrode shows an increase in the measured dissolved oxygen concentration, demonstrating the principle of the diagnostic.

The sensor design illustrated in FIG. 1 can be used to measure oxygen dissolved in the electrolyte.

Figure 5:
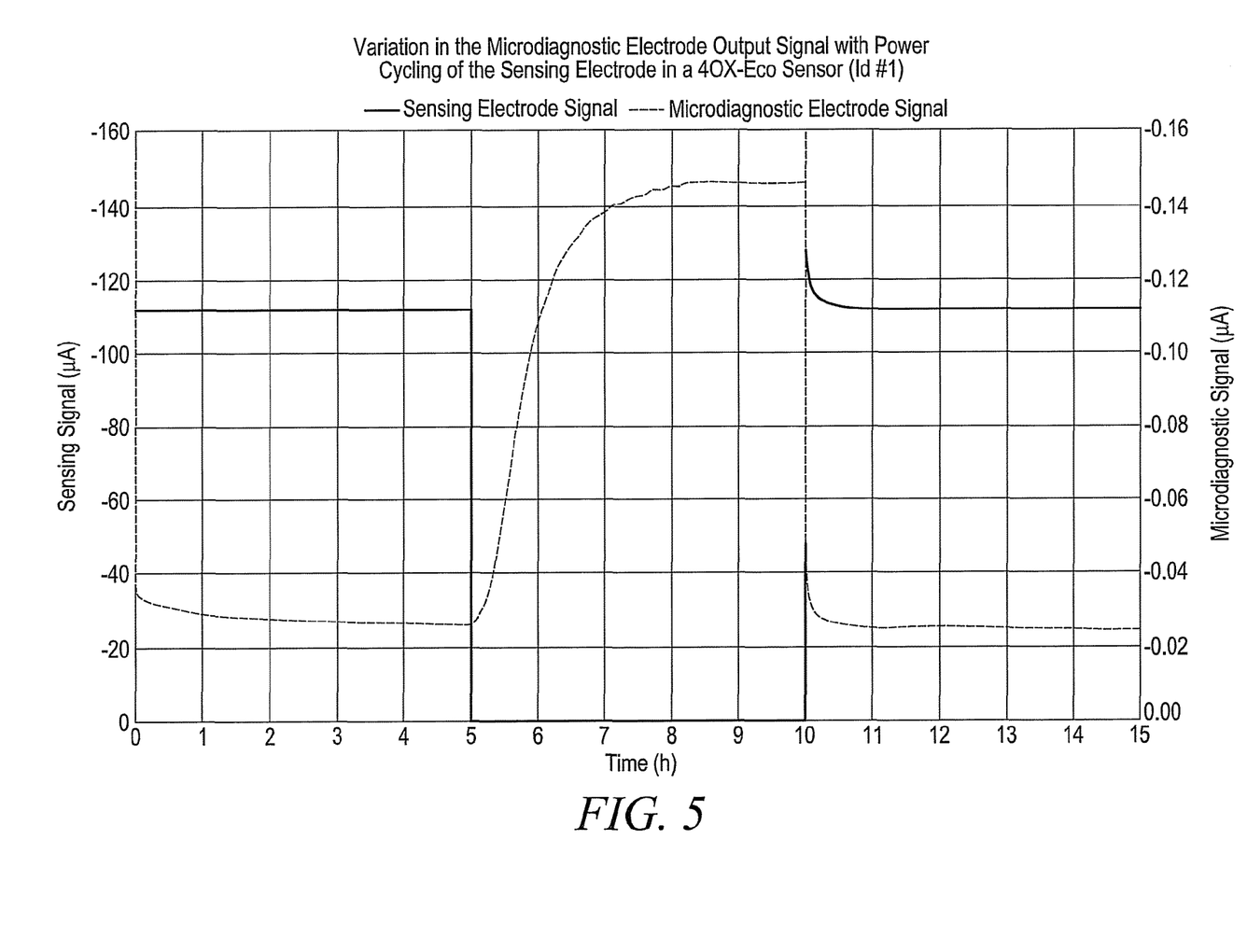
FIG. 5 illustrates a plot of micro-electrode output.

FIG. 5 illustrates the signals from the sensing electrode 20 and diagnostic micro-electrode 12 near the sensing electrode 20. Note the very different scales on the current axes for the two electrodes. The sensor 10 is operated in air, resulting in a diffusion limited signal of 110 uA on the sensing electrode 20, which is consuming almost all of the oxygen entering the sensor. After 5 hours the sensing electrode 20 is disconnected, its current drops to zero and it starts to allow oxygen to diffuse through it into the electrolyte.

The microelectrode 12, which was initially exhibiting a low background signal due to residual oxygen in the electrolyte, increases in signal as the oxygen diffuses to it through the electrolyte E. Due to the slow rate of diffusion of dissolved oxygen it takes several hours for the oxygen concentration and hence current to reach a steady state value, in this case about 0.15 microamps. At 10 hours, the sensing electrode 20 is reconnected and rapidly consumes oxygen from the electrolyte in its vicinity resulting in a relatively rapid drop in the microelectrode signal back to its background level.

The above described process demonstrates the ability of the micro-electrode 12 to detect a failure mode whereby the sensing electrode 20 fails to consume all of the target gas.

Similar methods could be employed to measure the oxygen concentration in the vicinity of the reference or counter electrodes 22, 24 arising from the passage of gas into the sensor through the primary diffusion barrier. For example, the counter electrode 24 in a toxic sensor requires oxygen for correct operation and the diagnostic electrode 14 can detect whether the oxygen level is too low. Reference electrodes such as Pt in $H_2SO_4$ have a potential which is dependent on local pH and oxygen concentration. It is normally the case that oxygen concentration is the dominant factor in determining potential in gas sensors. Thus, measurement of this parameter can be used to ensure that the reference is operating within acceptable bounds, or to compensate for undesirable shifts in reference potential.

Dissolved gases such as oxygen which have been generated within the sensor (e.g. produced from the counter electrode in oxygen pump sensors) or which have entered by routes other than the primary diffusion barrier (e.g. the pressure equalization vent if incorporated) can also be responsible for such undesirable effects. Thus, it can also be advantageous to establish diagnostic measurements capable of detecting these conditions.

Figure 6:
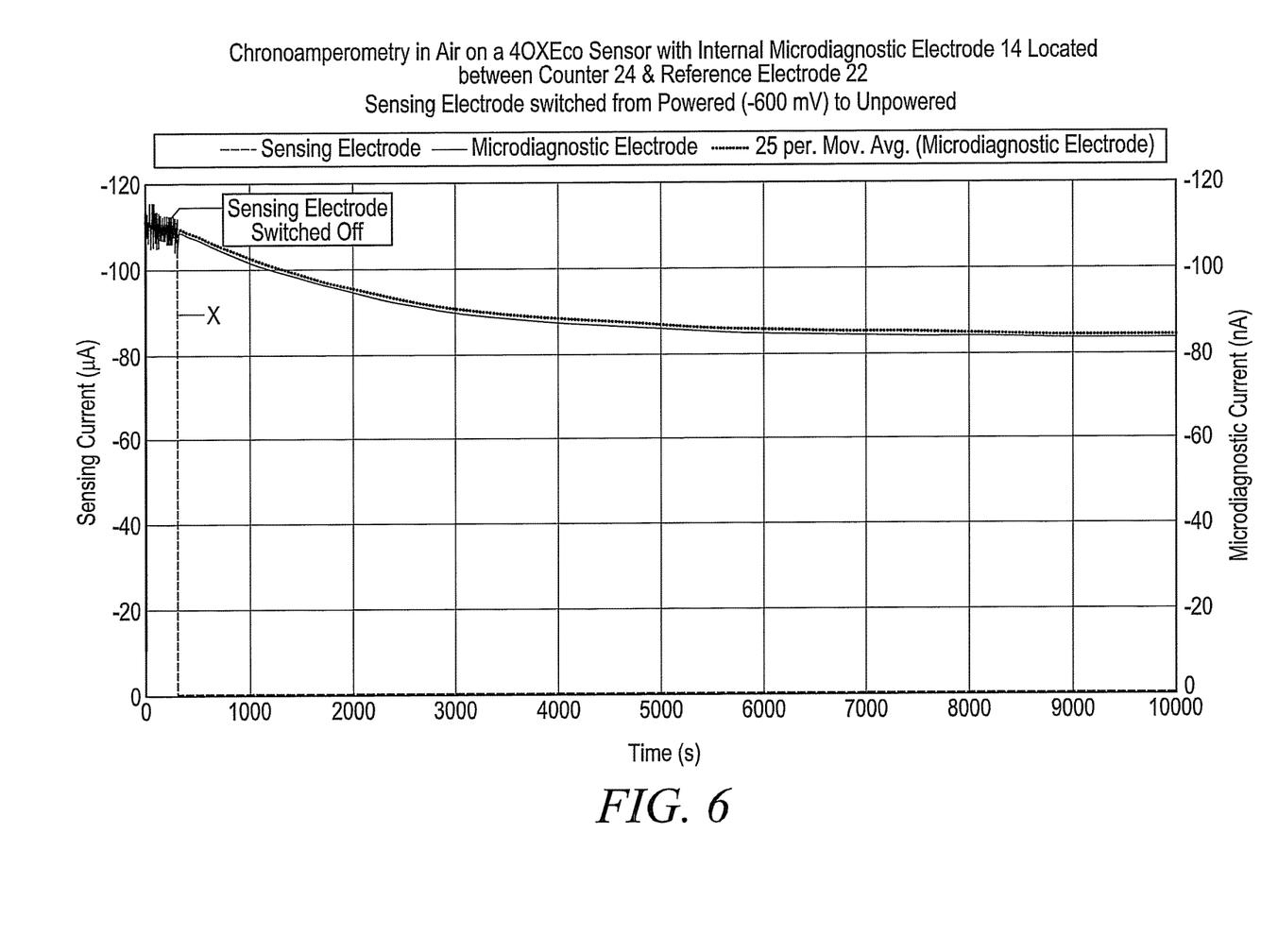
FIG. 6 illustrates a plot of output of a micro-electrode located between a counter and a reference electrode.

FIG. 6 illustrates a similar experiment but with a micro-electrode 14 in FIG. 1, near the counter electrode 24 where oxygen is generated by the sensor 10 during normal operation.

Initially as the sensor 10 is operating, oxygen is being consumed on the sensing electrode 20 and generated at the counter electrode 24 from where it mainly escapes through the vent 30. This also results in a buildup of dissolved oxygen in the vicinity of the counter electrode 24. At point x in FIG. 6 the sensing electrode 20 is switched off, and the counter electrode 24 stops generating oxygen. The microelectrode 14 initially measures a current of 110 nanoamps while the sensor 10 is running. When the sensor 10 is switched off the current at the microelectrode 14 decays down to a lower level of 85 nanoamps. This relatively large residual signal is believed to be due to oxygen from the ambient air entering from the vent 30. Such a measurement allows detection of issues such as where oxygen cannot easily escape from the sensor. For example a restricted vent may result in excessive buildup of dissolved oxygen near the counter electrode 24 and higher diagnostic signals during normal operation. Other dissolved species (such as ethanol) that may perturb the function of the sensor 10 can be similarly measured using the described method.

Conductivity tests can be carried out between the diagnostic micro-electrode and other electrodes in the sensor.

Notwithstanding the localized nature of the microelectrode action previously described, it is still possible to detect gross changes in electrode conductivity using these components. For example, the changes which will occur if there is inadequate electrical contact between any of the existing electrodes and its associated current collector can be detected. This is a potentially valuable diagnostic since intermittent or poor contacts are a known failure mode of some sensor designs.

A further advantage of the present micro-electrode approach is that such conductivity measurements can also be undertaken on a reference electrode. This would normally be ruled out by the disturbance due to the current passed, but by using a micro-electrode the current is reduced to such a small level that any disturbance of the reference electrode behavior is minimized to acceptable levels.

The micro-electrodes, such as 12, 14, can be used to generate gases to check the response of other electrodes in the sensor 10. Although the use of gas generated from electrodes to test the functionality of electrochemical sensors is known, the existing methods invariably rely on gas reaching the target electrode by diffusion through the gas phase. This may involve passage through the sensor diffusion barrier, or the generator may be inboard. However, the use of microelectrodes within the electrolyte E produces dissolved gases such as hydrogen or oxygen locally to the target electrode. Such gases can be used to examine different aspects of the functionality of those electrodes. For example, one might generate hydrogen from the electrode 12 close to a sensing electrode 20 to perform a simple activity test. Alternatively, one might generate oxygen near the reference electrode 22 to confirm that its potential is affected in accordance with the expectations of the design and that its operation is normal.

Micro-electrode based DHE can be used intermittently in checking drift. We have recognized that basing a DHE on a microelectrode as described here enables this method to also be employed as an intermittent means of checking for drift in the potential of the existing reference electrode.

In order to minimize current (and hence power requirements) and also to minimize the amount of hydrogen generated (which could potentially interfere with the rest of the sensor) it is desirable to use a very small surface area for the DHE electrode. For example, to obtain the usual DHE current density of 1 mA/cm2 with a disc microelectrode of 100 um diameter only requires 80 nA. Another reason for keeping the current low is that the DHE reaction, whether in acid or alkaline electrolyte, involves the electrolysis of water with 2 moles of water consumed per mole of hydrogen gas produced. In practice a DHE current of 1 uA results in an electrolysis rate of 6 mg of water per year. Given that typical water uptake or loss rates in gas sensors in ambient conditions are of the order of 100 to 1000 mg per year, the additional loss due to this DHE current is negligible. Even electrolysis rates orders of magnitude higher may be acceptable as the sensor's electrolyte E will always tend to compensate in response to the ambient conditions. The reference electrode 22 does not need to be platinum (as commonly used for DHE electrodes) but could be palladium. The latter has the benefit of being able to adsorb hydrogen so could be powered intermittently to generate hydrogen then run without imposed current.

Also, with both platinum and palladium, it is not strictly necessary to generate gaseous hydrogen. It may be sufficient to simply generate adsorbed hydrogen which requires a lower current and minimizes issues with generated gas. One potential issue with the generation of gases such as hydrogen within the sensor is that if these gases reach other electrodes they may result in interfering signals on those electrodes. This effect is minimized by the use of a sufficiently small gas generating electrode, i.e. keeping the amount of gas generated to a minimum, but can also be reduced further by arranging suitable scavenging electrodes that sandwich the gas generating electrode or screen other electrodes preventing the generated hydrogen from reaching them.

It is not necessary for the reference electrode 22 to generate its own hydrogen—although this is the usual way a dynamic hydrogen electrode operates. It is also possible for one electrode to generate hydrogen which is fed to a nearby second electrode which acts as the hydrogen electrode.

An example of the application of several of the above approaches all run on a single microelectrode is in the localised measurement of electrolyte pH. This can be important since a number of common reaction mechanisms are pH dependent. The first step to achieve this is to use one of the previously described approaches to accurately calibrate the existing sensor pseudo-reference electrode potential. The same microelectrode is then used to obtain a local measurement of the dissolved oxygen concentration, again as previously described. Finally, the same (or an additional nearby microelectrode) is allowed to reach its open circuit potential which is itself a known function of both pH and dissolved oxygen concentration. This is measured against the previously calibrated pseudo-reference. The resulting measurements can be used to infer local pH at the microelectrode.

Figure 7:
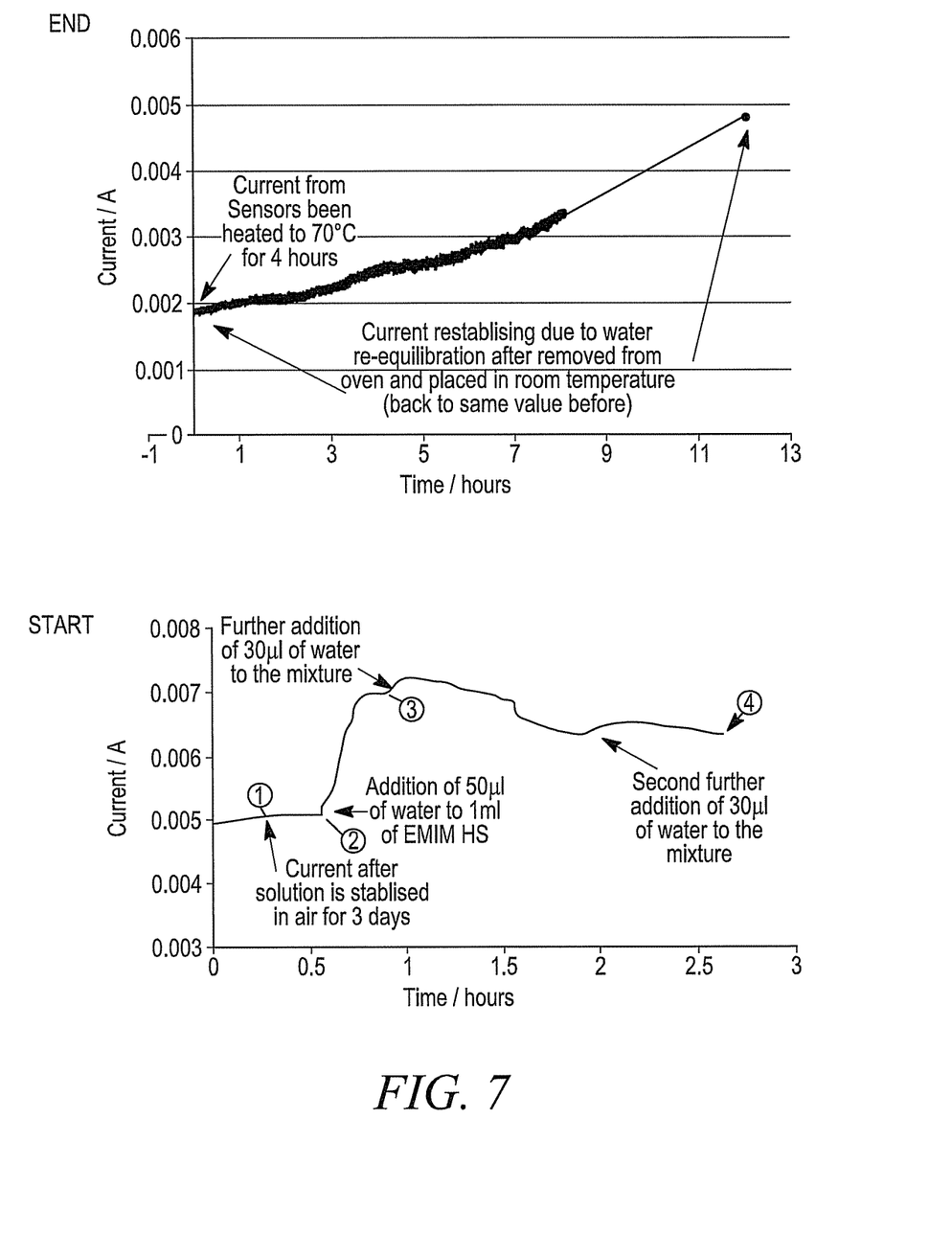
FIG. 7 illustrates measurements of water content of a relatively hydrophobic electrolyte.

The water content of an ionic liquid electrolyte can be measured using micro-electrodes. FIG. 7 illustrates the use of a microdiagnostic electrode to measure water content of a relatively hydrophobic electrolyte, in this case a commercially available ionic liquid, 1-Ethyl-3-methylimidazolium hydrogensulfate (CAS number 412009-61-1). The diagnostic electrode used in this case was a bare platinum wire of 50 um diameter and 5 mm length within the electrolyte, without any insulation. In this configuration, it behaves as a micro-cylinder electrode.

The data was generated using an arrangement similar to that shown in the lower part of FIG. 1. The sensor base, pins and associated current collector wires 10-1 were used to provide a convenient means to undertake tests on electrolytes placed into the chamber formed by the base. The current collector wires thus acted as the cylindrical microelectrodes. In an alternate implementation, microelectrodes of the type previously described could be used within the stack arrangement.

The diagnostic electrode can be biased to +5V vs. the platinum pseudo reference electrode. This configuration is sufficient to ensure that it is within the oxygen evolution region due to water breakdown, and provides a signal which is diffusion limited and hence proportional to the water concentration within the electrolyte.

Initially the electrolyte (1 ml volume) is relatively dry (equilibrated with ambient air). This results in a small signal of 5 milliamps (region 1 in the chart). At point (2) 50 microL of water is added to the electrolyte. The signal on the microelectrode is seen to increase to 7.1 milliamps. A further addition of 30 microL of water at point (3) results in a further increase in signal to 7.4 milliamps.

At point (4) the system was disconnected from the potentiostat and heated to 70 C in an oven to dry out the electrolyte, and then returned to ambient conditions and reconnected to the potentiostat. The current decreased to 1.9 milliamps and then gradually increases due to ambient humidity reabsorbing into the electrolyte. Overnight the current returns to 5 mA as the electrolyte water content re-equilibrates with the ambient air.

In practice the currents observed here are relatively large due to a relatively large surface area bare wire being used, however if a micro disc electrode of the type shown in FIG. 1 were used the currents would be much lower. The diffusion coefficient of water within the ionic liquid is itself likely to be a function of the water concentration. Thus, the response is not necessarily linear with concentration but will be repeatable and can be calibrated for a particular electrolyte system. In practice, the electrical signal indicating the effect of temperature upon the diffusion coefficient can be compensated as needed. Other methods of operating the electrode such as transient methods such as voltammetry or potential steps could also be used.

Measuring the water content of electrolytes such as ionic liquids is beneficial since many of their properties (conductivity, viscosity, gas solubility, reference potential, etc.) can vary significantly with water content resulting in variation in performance of a gas sensor using them. Thus it is possible to check for or compensate for such variations.

Ionic Liquids are not the only class of electrolyte which could benefit from this form of diagnostic. Any system where water is a minor component could in principle be probed in a similar way. The method is of less value in electrolytes which are fundamentally aqueous in nature (e.g. $H_2SO_4$) since their much higher water contents will generate very large currents which are not a useful indicator of hydration level.

In accordance with the above, the diagnostic electrode(s) is/are implemented as micro-electrodes to minimize interference with the operation of the sensing electrode 20 as well as other electrodes or elements in the sensor. In one aspect, the area of the micro-electrodes is at least an order of magnitude less than the area of the sensing electrodes. Preferably, the area of the micro-electrodes is at least two orders of magnitude, or more, smaller than the areas of the sensing electrodes. The micro-electrodes as disclosed above operate substantially, completely independently of the sensing electrodes.

Diagnostic, or micro-electrodes as disclosed above can be incorporated into liquid electrolyte-based electrochemical gas sensors including, without limitation, toxic gas sensors, oxygen pumps, as well as consumable anode oxygen sensors. The diagnostic electrode(s) is/are immersed in the electrolyte and are not in direct communication with the incoming target gas which is passing through the diffusion barrier that controls access to the sensing electrodes.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A gas sensor comprising:
    a housing comprising an internal gas sensing cavity;
    a liquid electrolyte;
    plurality of electrodes arranged in a stacked configuration within the housing, wherein the plurality of electrodes comprise at least one sensing electrode, a reference electrode, and a counter electrode; and
    at least one microelectrode, wherein the at least one microelectrode is positioned between the at least one sensing electrode and the counter electrode in the stacked configuration, and wherein the at least one microelectrode comprises a surface area that is at least one order of magnitude smaller than a surface area of the at least one sensing electrode.

2. A gas sensor as in claim 1, wherein the plurality of electrodes and the at least one microelectrode are coupled to control circuits, and wherein the control circuits are configured to carry out at least one diagnostic function using the at least one microelectrode.

3. A gas sensor as in claim 1, which includes a plurality of diagnostic micro-electrodes immersed in the electrolyte.

4. A gas sensor as in claim 2, where the diagnostic function is a member of a class which includes at least detecting functionality of the at least one sensing electrode, or generating a test gas to provide a stimulus for the at least one sensing electrode.

5. A gas sensor as in claim 2, wherein the diagnostic function is a member of a class which includes at least measuring oxygen concentration in the electrolyte in the gas sensor in the vicinity of the reference electrode, measuring a redox couple dissolved in the electrolyte, or measuring drift in the reference electrode potential.

6. A gas sensor as in claim 2, wherein the diagnostic function is a member of a class which includes at least one of: detecting functionality of the at least one sensing electrode, generating a test gas to provide a stimulus for the at least one sensing electrode, measuring oxygen concentration in the electrolyte in the gas sensor in the vicinity of the reference electrode, measuring a redox couple dissolved in the electrolyte, measuring drift in the reference electrode potential, locally producing a selected gas dissolved in the electrolyte in the vicinity of at least one of the sensing electrode, the counter electrode, or the reference electrode, or measuring water content of the electrolyte.

7. A gas sensor as in claim 6, wherein the at least one microelectrode has a first exposed area and the at least one sensing electrode has a second exposed area, and wherein the second exposed area is greater than the first exposed area.

8. A gas sensor as in claim 7, wherein the at least one microelectrode is shaped as one of a conducting cylinder or a conducting disk.

9. A gas sensor as in claim 6, wherein the control circuits are configured to operate the at least one microelectrode, at least intermittently.

10. A gas sensor as in claim 1, wherein the plurality of electrodes and the at least one microelectrode are coupled to control circuits, and wherein the control circuits are configured to carry out at least one diagnostic function using the at least one microelectrode while the gas sensor is sensing a target gas.

11. A gas sensor as in claim 2, wherein the surface area of the at least one sensing electrode is at least two orders of magnitude greater than the surface area of the at least one microelectrode.

12. The gas sensor of claim 1, wherein the stacked configuration comprises the reference electrode disposed between the at least one sensing electrode and the counter electrode.

13. The gas sensor of claim 12, wherein the at least one microelectrode is disposed between the reference electrode and the counter electrode in the stacked configuration.

14. The gas sensor of claim 1, further comprising: a metallic wire with an insulating coating, wherein a portion of the insulating coating is absent, and wherein a portion of the metallic wire is exposed at the absent portion of the insulating coating, wherein the portion of the metallic wire that is exposed is the at least one microelectrode.

15. The gas sensor of claim 14, wherein the metallic wire comprises platinum.

16. The gas sensor of claim 15, wherein the insulating coating comprises a polytetrafluoroethylene (PTFE) coating.

17. A gas detector comprising:
a housing;
a gas sensor carried by the housing, the gas sensor including at least a sensing electrode, an electrolyte, and at least one diagnostic electrode immersed in the electrolyte, wherein the at least one diagnostic electrode has a first exposed area and the sensing electrode has a second exposed area, and wherein the second exposed area is at least an order of magnitude greater than the first exposed area; and
control circuits carried, at least in part in the housing, wherein the control circuits are coupled to the electrodes of the gas sensor, and wherein the control circuits are configured to:
operate the at least one diagnostic electrode, at least intermittently while the at least one sensing electrode is functioning to sense a target gas, to carry out a diagnostic function selected from a class which includes at least, detecting functionality of the at least one sensing electrode, generating a test gas to provide a stimulus for the at least one sensing electrode, measuring oxygen concentration in the electrolyte in the sensor in the vicinity of a reference electrode, measuring a redox couple dissolved in the electrolyte, measuring drift in the reference electrode potential, locally producing a selected gas dissolved in the electrolyte in the vicinity of at least one of the at least one sensing electrode, a counter electrode, or the reference electrode, or measuring water content of the electrolyte.

18. A gas detector as in claim 17, further comprising s diffusion barrier, where the at least one sensing electrode is in direct fluid communication with the diffusion barrier.

* * * * *

UNITED STATES PATENT AND TRADEMARK OFFICE
CERTIFICATE OF CORRECTION

PATENT NO. : 9,689,833 B2  
APPLICATION NO. : 13/644485  
DATED : June 27, 2017  
INVENTOR(S) : Keith Francis Edwin Pratt et al.

Page 1 of 1

It is certified that error appears in the above-identified patent and that said Letters Patent is hereby corrected as shown below:

In the Specification

Column 7, Line 4: "I/R" should be "IR"

Column 7, Line 12: "1000" should be "100"

In the Claims

Column 12, Line 42: insert --a-- before "plurality"

Column 13, Line 11: "drill" should be "drift"

Column 14, Line 40: "s" should be "a"

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*